United States Patent
Roeder et al.

(10) Patent No.: US 8,523,932 B2
(45) Date of Patent: Sep. 3, 2013

(54) VARIABLE DIAMETER TRIGGER WIRE

(75) Inventors: Blayne A. Roeder, Lafayette, IN (US); Alan R. Leewood, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 392 days.

(21) Appl. No.: 12/786,109

(22) Filed: May 24, 2010

(65) Prior Publication Data
US 2011/0288624 A1 Nov. 24, 2011

(51) Int. Cl.
*A61F 2/06* (2006.01)
(52) U.S. Cl.
USPC ............ 623/1.11; 623/1.12; 623/1.13
(58) Field of Classification Search
USPC ........ 623/1.11, 1.12, 1.13; 606/108; 604/36, 604/48, 507, 264
See application file for complete search history.

(56) References Cited

U.S. PATENT DOCUMENTS

| | | | | |
|---|---|---|---|---|
| 4,813,934 | A * | 3/1989 | Engelson et al. | 604/99.02 |
| 5,404,887 | A * | 4/1995 | Prather | 600/585 |
| 5,800,517 | A * | 9/1998 | Anderson et al. | 623/1.11 |
| 5,946,779 | A * | 9/1999 | Chen | 24/712 |
| 5,964,771 | A | 10/1999 | Beyar et al. | |
| 6,019,779 | A * | 2/2000 | Thorud et al. | 606/198 |
| 6,280,464 | B1 | 8/2001 | Hayashi | |
| 6,371,953 | B1 * | 4/2002 | Beyar et al. | 623/1.1 |
| 6,960,227 | B2 | 11/2005 | Jones et al. | |
| 7,470,282 | B2 | 12/2008 | Shelso | |
| 2003/0171642 | A1 * | 9/2003 | Schock et al. | 600/18 |
| 2004/0073289 | A1 | 4/2004 | Hartley | |
| 2005/0038503 | A1 | 2/2005 | Greenhalgh et al. | |
| 2005/0055077 | A1 | 3/2005 | Marco et al. | |
| 2006/0020319 | A1 | 1/2006 | Kim et al. | |
| 2006/0142704 | A1 | 6/2006 | Lentz | |
| 2007/0021822 | A1 | 1/2007 | Boatman | |
| 2007/0060846 | A1 * | 3/2007 | Hardin | 600/585 |
| 2007/0233222 | A1 * | 10/2007 | Roeder et al. | 623/1.11 |
| 2008/0027481 | A1 | 1/2008 | Gilson et al. | |
| 2008/0027529 | A1 * | 1/2008 | Hartley et al. | 623/1.11 |
| 2008/0140178 | A1 * | 6/2008 | Rasmussen et al. | 623/1.11 |

(Continued)

FOREIGN PATENT DOCUMENTS

| | | |
|---|---|---|
| WO | WO 2007/100716 A2 | 9/2007 |
| WO | WO 20071142962 A2 | 12/2007 |
| WO | WO 2010/042210 A1 | 4/2010 |

OTHER PUBLICATIONS

PCT Search Report and Written Opinion in related application No. PCT/US2011/036587 (PA-6709-PCT), mailing date Oct. 6, 2011.

*Primary Examiner* — Gary Jackson
*Assistant Examiner* — Richard Louis
(74) *Attorney, Agent, or Firm* — Brinks Hofer Gilson & Lione

(57) ABSTRACT

A self-expanding medical device delivery system includes a plurality of trigger wires. The trigger wires retain a self-expanding medical device by forming a bend about structural members located on the proximal portion of the medical device. The proximal portions of the trigger wires have a greater diameter than the distal portions of the trigger wires to provide increased bending strength. An operator releases the self-expanding medical device by withdrawing the trigger wires in the distal direction. In some embodiments, a small portion at the proximal end of each trigger wire has a smaller diameter than the rest of the proximal portion. In other embodiments, the proximal and distal portions of each trigger wire each have a greater diameter than the center of the trigger wire.

19 Claims, 6 Drawing Sheets

(56) References Cited

U.S. PATENT DOCUMENTS

| | | |
|---|---|---|
| 2009/0030497 A1 | 1/2009 | Metcalf et al. |
| 2009/0082842 A1* | 3/2009 | Glynn .......................... 623/1.11 |
| 2009/0099594 A1 | 4/2009 | Brady |
| 2009/0105753 A1* | 4/2009 | Greenhalgh et al. .......... 606/228 |
| 2009/0204202 A1 | 8/2009 | Dierking et al. |
| 2009/0228093 A1* | 9/2009 | Taylor et al. ................. 623/1.12 |
| 2010/0152752 A1* | 6/2010 | Denove et al. ................ 606/148 |
| 2012/0022630 A1* | 1/2012 | Wubbeling .................. 623/1.11 |

* cited by examiner

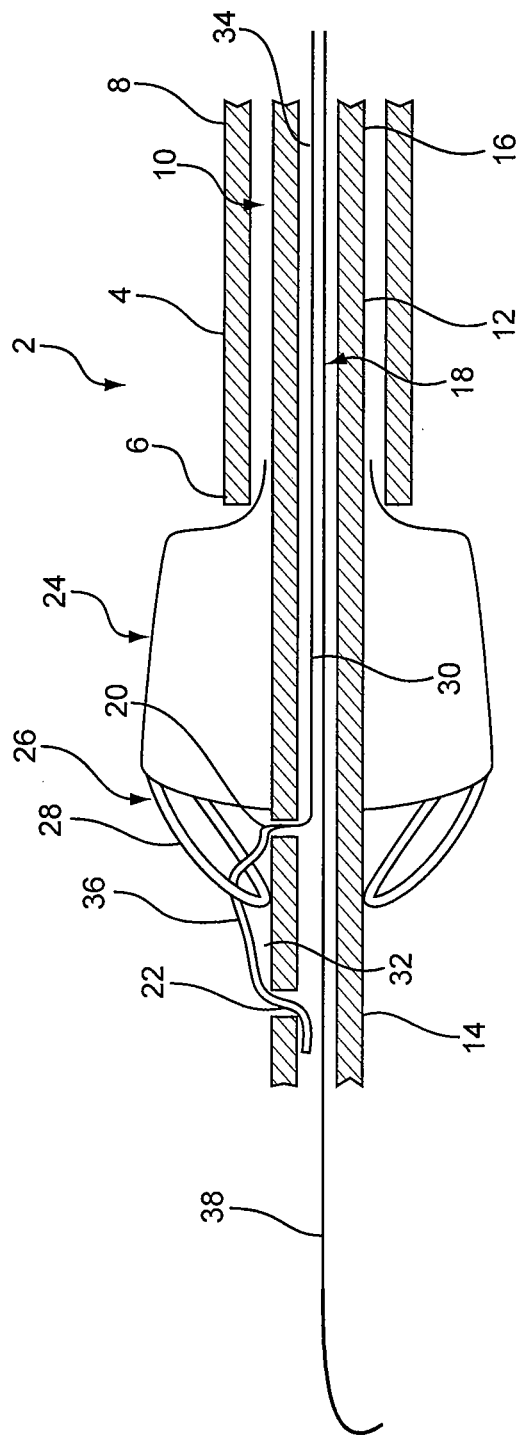
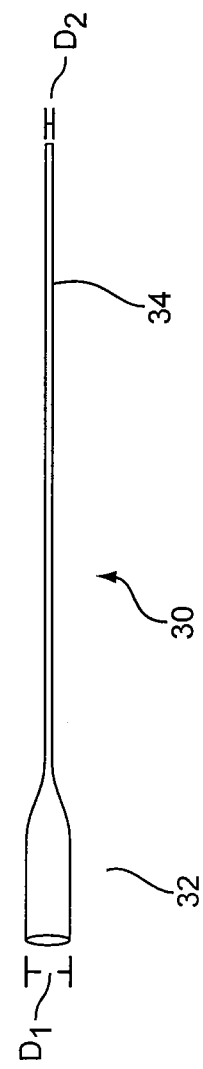
Fig.1
Fig.2

VARIABLE DIAMETER TRIGGER WIRE

BACKGROUND

The present invention relates generally to medical device deployment systems and more particularly to trigger wires used in low-profile delivery systems for self-expanding medical devices.

The use of trigger wires in delivery systems to retain and release self-expanding medical devices is well-known in the art. As used in the present application, "proximal" and "distal" are defined relative to the heart. Trigger wires typically retain a self-expanding medical device by forming a bend around a portion of the self-expanding medical device, and release the self-expanding medical device when the trigger wire is withdrawn proximally through the delivery system so that the trigger wire no longer forms a bend about the medical device. Known trigger wires are of constant cross-section. Thus, trigger wires must restrain the self-expanding medical device during delivery, be capable of being withdrawn through the delivery system, and provide an adequate connection to a handle at the distal end of the trigger wire.

Different levels of bending and tensile strength are required for each of the functions a trigger wire must perform. For example, a certain level of bending strength is required at the proximal portion of the trigger wire where the trigger wire retains the medical device, and a certain level of bending strength is also required at the distal portion of the trigger wire where the trigger wire connects to the handle. The center portion of the trigger wire only requires adequate tensile strength as an operator withdraws the trigger wire through the delivery system.

Delivery devices for self-expanding medical devices are typically advanced through a body vessel to a treatment site. Thus, it is advantageous to minimize the size of delivery devices to allow operators to place self-expanding medical devices in smaller body vessels, and to minimize potential trauma to body vessels as the delivery device passes through. A lower-profile device is also advantageous because it is easier to navigate through tortuous vasculature. Additionally, a lower-profile delivery device is advantageous to allow an operator to position or use other medical devices in the body vessel simultaneously with the delivery device.

BRIEF SUMMARY

The invention may include any of the following aspects in various combinations and may also include any other aspect described below in the written description or in the attached drawings.

A self-expanding medical device delivery system includes a delivery sheath and an inner member, where the inner member is disposed within the lumen of the delivery sheath. A plurality of first openings and a plurality of second openings are disposed on the proximal portion of the inner member. A self-expanding medical device is also disposed upon the proximal portion of the inner member. The proximal portion of the self-expanding medical device includes exposed structural members. A plurality of trigger wires is disposed within the lumen of the inner member, each trigger wire exiting the lumen of the inner member through a first opening and re-entering the lumen through a second opening, thereby forming a bend. The proximal portion of the trigger wires has a greater diameter than the distal portion of the trigger wires. The bends formed by the trigger wires engage and compress the exposed structural members of the self-expanding medical device toward the inner member, retaining the self-expanding medical device on the inner member. To deploy the self-expanding medical device, an operator withdraws the trigger wires through the lumen of the inner member until the proximal portions of the trigger wires no longer pass through the second openings.

The diameter of the proximal portion of the trigger wire may be five times the diameter of the distal portion of the trigger wire.

The self-expanding medical device deployed may be a stent graft or a self-expanding stent.

The delivery system may also include a guide wire which passes through the lumen of the delivery sheath and extends beyond the most proximal portion of the inner member.

The first and second openings may be positioned at varying distances from the distal end of the inner member.

The proximal end of the inner member may be flared outward.

The proximal end of the trigger wire may have a smaller diameter than the proximal portion of the trigger wire.

Alternatively, the plurality of trigger wires may have a proximal portion, a distal portion, and a center portion. The diameter of the proximal portion of the trigger wire is greater than the diameter of the center portion of the trigger wire. The diameter of the distal portion of the trigger wire is also greater than the diameter of the center portion of the trigger wire. The distal portions of the trigger wires are attached to a handle configured to withdraw the trigger wires in the distal direction through the lumen of the inner catheter to release the self-expanding medical device.

The diameter of the distal portion of the trigger wire may be five times the diameter of the center portion of the trigger wire.

The proximal end of the trigger wire may have a smaller diameter than the proximal portion of the trigger wire.

BRIEF DESCRIPTION OF THE DRAWINGS

FIG. 1 is a longitudinal section view of the self-expanding medical device delivery system and one of the plurality of trigger wires partially deployed.

FIG. 2 is a longitudinal view of one embodiment of the trigger wires.

DETAILED DESCRIPTION OF THE DRAWINGS AND THE PRESENTLY PREFERRED EMBODIMENTS

Figure 3:
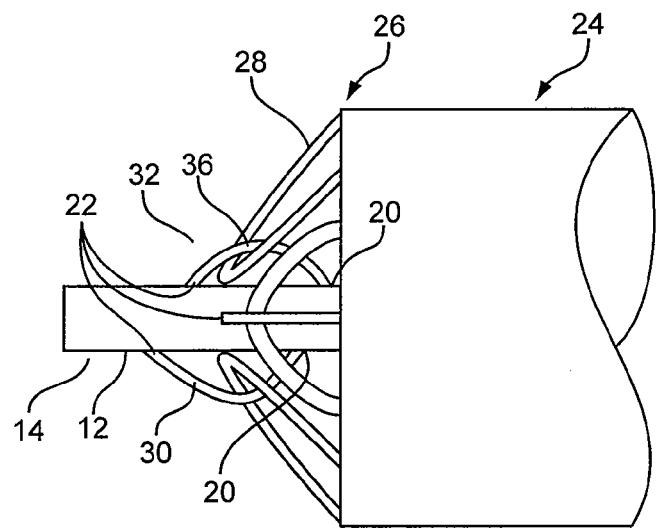
FIG. 3 is a partial longitudinal view of the self-expanding medical device delivery system wherein the self-expanding medical device is partially deployed and constrained by a plurality of trigger wires.

Referring now to the figures, a self-expanding medical device delivery system is shown. A delivery sheath 4 has a lumen 10. An inner member 12 is disposed within the lumen 10 of the delivery sheath 4. A plurality of first openings 20 and a plurality of second openings 22 are disposed upon the proximal portion 14 of inner member 12. Each of the second openings of the plurality of second openings 22 is disposed proximally of one of the openings of the plurality of first openings 20.

A self-expanding medical device 24 is disposed about the proximal portion 14 of inner member 12. The proximal end 26 of self-expanding medical device 24 includes exposed structural members 28. Self-expanding medical device 24 may be a self-expanding stent, stent graft, or any other self-expanding medical device that includes exposed structural members.

A plurality of trigger wires 30 is disposed within the lumen 18 of inner member 12. Each of the trigger wires of the plurality of trigger wires 30 has a proximal portion 32 and a distal portion 34. The proximal portion 32 of each of the trigger wires of the plurality of trigger wires 30 has a greater diameter than the diameter of distal portion 34. Each of the trigger wires of the plurality of trigger wires 30 exits the lumen 18 of inner member 12 through one of the openings of the plurality of first openings 20 and re-enters the lumen 18 of inner member 12 through one of the openings of the plurality of second openings 22 such that the proximal portion 32 of each of the trigger wires of the plurality of trigger wires 30 forms a bend 36. The transition between the first and second diameters preferably occurs within one of the openings of the plurality of first openings 20. Bend 36 engages and compresses exposed structural members 28 toward inner member 12, retaining self-expanding medical device 24 in position on the proximal portion 14 of inner member 12.

Each of the trigger wires of the plurality of trigger wires 30 may be tapered using any of a number of suitable manufacturing methods. For example, the distal portion 34 of the each of the trigger wires of the plurality of trigger wires 30 could be ground to reduce its diameter. Another method for tapering each of the trigger wires of the plurality of trigger wires 30 would be to overlay a thin cannula over the proximal portion 32 of each of the trigger wires of the plurality of trigger wires 30. Other methods not described here may also be used.

Figure 4:
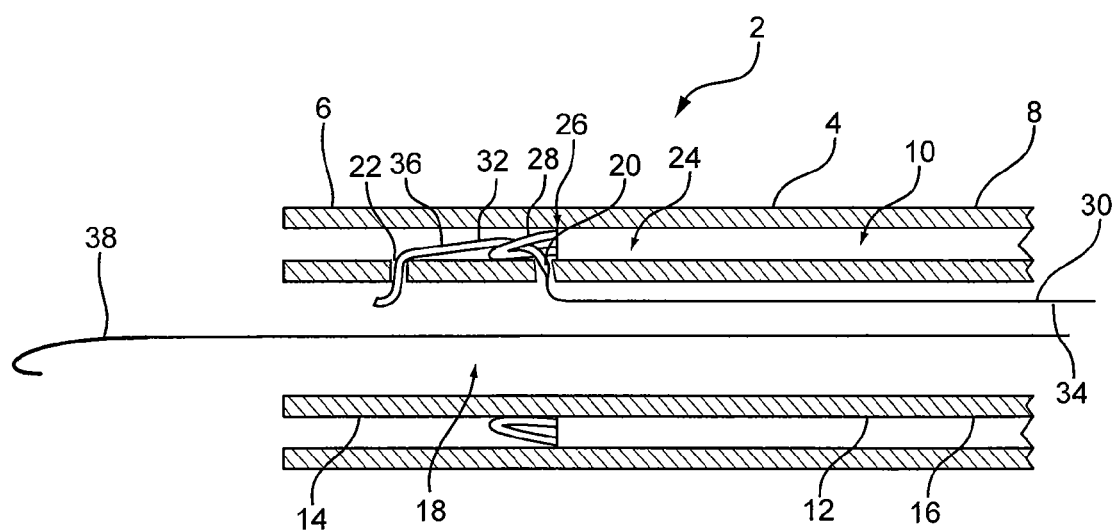
FIG. 4 is a longitudinal section view of the self-expanding medical device delivery system and one of the plurality of trigger wires in its delivery configuration.

Each of the trigger wires of the plurality of trigger wires 30 is configured to be withdrawn in the distal direction through the lumen 18 of inner member 12. To deploy self-expanding medical device 24, an operator advances self-expanding medical device delivery system 2 through a body vessel to a desired deployment site. The device is advanced in its delivery configuration as shown in FIG. 4. As the operator advances the device to the deployment site, the delivery sheath 4 covers the inner member 12 and self-expanding medical device 24. After positioning self-expanding medical device 24 at the desired location, the operator withdraws the delivery sheath 4 in the distal direction to expose the proximal portion 14 of inner member 12 and the self-expanding medical device 24 as shown in FIG. 1. The operator then withdraws each of the trigger wires of the plurality of trigger wires 30 through lumen 18 of inner member 12. The operator may withdraw each of the plurality of trigger wires 30 individually through the lumen 18 of inner member 12 or withdraw each of the plurality of trigger wires 30 through the lumen 18 of inner member 12 at different rates. As each of the trigger wires of the plurality of trigger wires 30 is withdrawn, proximal portion 32 of each of the trigger wires of the plurality of trigger wires 30 is pulled out of one of the openings of the plurality of second openings 22 until proximal portion 32 no longer passes through one of the openings of the plurality of second openings 22. When proximal portion 32 is removed from one of the openings of the plurality of second openings 22, exposed structural members 28 are no longer restrained by proximal portion 32 of each of the trigger wires of the plurality of trigger wires 30. The exposed structural members 28 expand outward to anchor self-expanding medical device 24 at the location desired by the operator.

This configuration allows the use of a delivery sheath 4 and inner member 12 with smaller diameters than used with a trigger wire of a constant diameter. Because the proximal portion 32 of each of the trigger wires of the plurality of trigger wires 30 is disposed proximally of the proximal end 26 of self-expanding medical device 24, self-expanding medical device 24 may be more fully compressed. Additionally, inner member 12 need only be large enough to allow the operator to withdraw one of the trigger wires of the plurality of trigger wires 30 through the lumen 18 of inner member 12.

Figure 8:
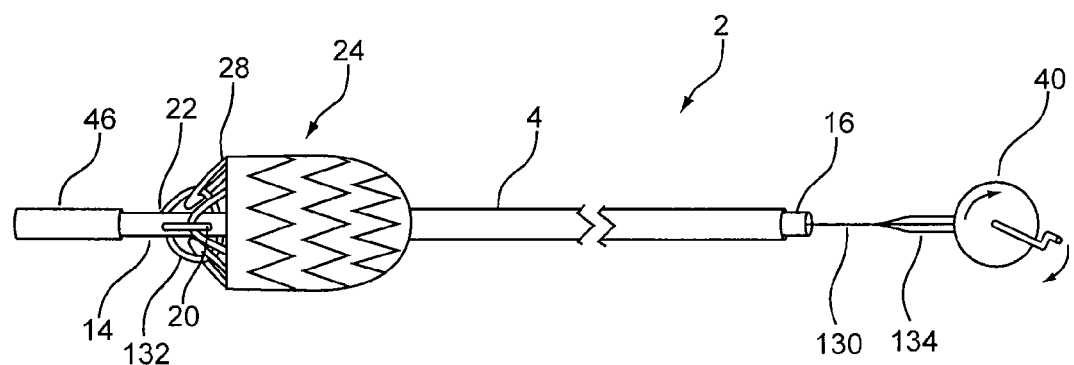
FIG. 8 is a longitudinal view of the partially deployed self-expanding medical device delivery system where the trigger wires have a larger diameter at the proximal and distal ends.

As shown in FIG. 1, the self-expanding medical device delivery system 2 may include the use of a guide wire 38. The self-expanding medical device delivery system 2 may also include a bulbous tip 46, as shown in FIG. 8.

As shown in FIG. 3, the self-expanding medical device 24 may be a stent graft. A plurality of trigger wires 30 is shown retaining the self-expanding medical device 24 on inner member 12, as shown in FIG. 3. Each of the openings of the plurality of first openings 20 and each of the openings of the plurality of second openings 22 may be staggered such that each of the trigger wires of the plurality of trigger wires 30 enters and exits the inner member 12 at different longitudinal positions. This allows the inner member 12 to be of a smaller diameter, because each of the proximal portions 32 of each of the trigger wires of the plurality of trigger wires 30 are staggered such that at least one proximal portion 32 does not lie parallel to at least one other proximal portion 32 as the plurality of trigger wires 30 is withdrawn.

Proximal portion 32 of each of the trigger wires of the plurality of trigger wires 30 has a diameter that can provide adequate strength to retain self-expanding medical device 24. Thus, the diameter of the proximal portion 32 is dependent upon the type of self-expanding medical device 24 used. In the embodiment shown in FIG. 3, self-expanding medical device 24 is a stent graft. The diameter of the proximal portion 32 required to retain a common stent graft may range from 2 to 5 times the diameter of the distal portion 34. The proximal portion 32 of each of the trigger wires of the plurality of trigger wires 30 must be long enough to form a bend 36 around the exposed structural members 28. For a typical stent graft, the proximal portion 32 may be 1 to 2 inches long.

In contrast, distal portion 34 of each of the trigger wires of the plurality of trigger wires 30 only requires adequate tensile strength to withdraw each of the trigger wires of the plurality of trigger wires 30 through lumen 18 of inner member 12. Thus, the required diameter of distal portion 34 is less than the diameter of proximal portion 32. By providing each of the trigger wires of the plurality of trigger wires 30 with a distal portion 34 of lesser diameter than proximal portion 32, a smaller inner member 12 may be used. In turn, this allows the use of a smaller diameter delivery sheath 4, which would result in a self-expanding medical device delivery system 2 with a lower profile. The distal portion 34 of each of the trigger wires of the plurality of trigger wires 30 must be long enough to extend from the deployment site through the vasculature and outside the body to the operator. Thus, the distal portion 34 may be up to 3 feet long.

Figure 5:
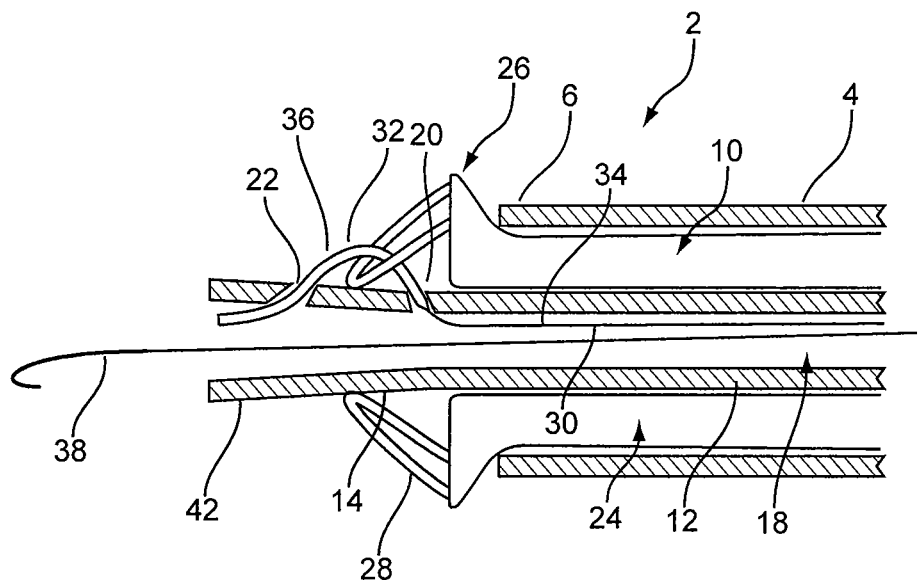
FIG. 5 is a longitudinal section view of the partially-deployed self-expanding medical device delivery system with a flared portion at the proximal end of the inner member.

FIG. 5 illustrates another embodiment of the self-expanding medical device delivery system 2. In this embodiment, the proximal end 42 of the proximal portion 14 of the inner member 12 is flared outward to receive the proximal portion 32 of each of the trigger wires of the plurality of trigger wires 30. Because the flared proximal end 42 is proximal to the self-expanding medical device 24, a smaller delivery sheath 4 may be used.

Figure 6:
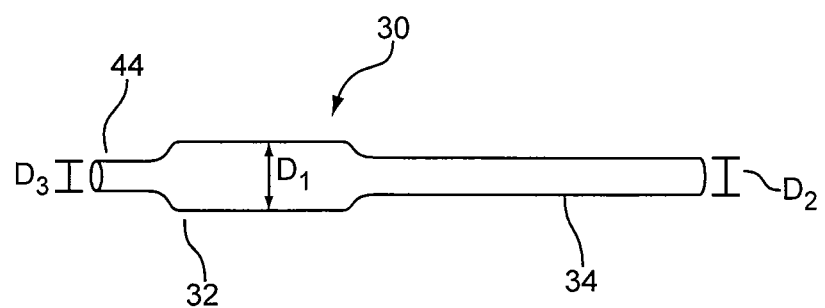
FIG. 6 is a longitudinal view of another embodiment of the plurality of trigger wires wherein the proximal ends of the trigger wires have a smaller diameter than the diameter of the proximal portions of the trigger wires.
Figure 7:
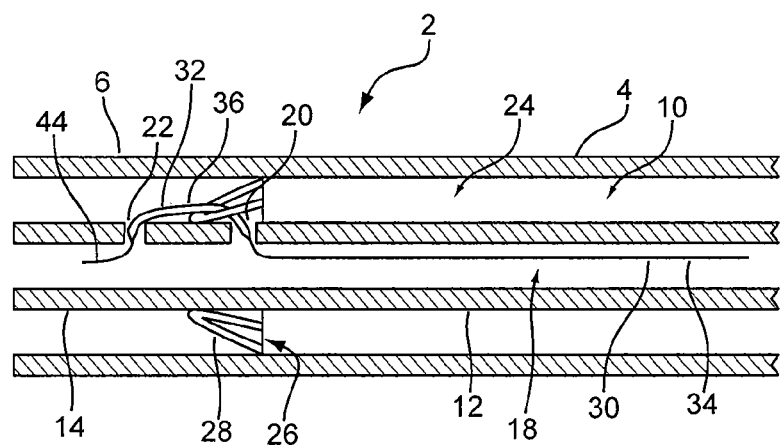
FIG. 7 is a longitudinal section view of self-expanding medical device delivery system with the trigger wires shown in FIG. 6.

FIGS. 6 and 7 illustrate another embodiment of the each of the trigger wires of the plurality of trigger wires 30. In this embodiment, the proximal end 44 of the each of the trigger wires of the plurality of trigger wires 30 has a smaller diameter than the diameter of the proximal portion 32 of each of the trigger wires of the plurality of trigger wires 30. The proximal end 44 of each of the trigger wires of the plurality of trigger wires 30 is the portion of each of the trigger wires of the plurality of trigger wires 30 that re-enters inner member 12 through one of the openings of the plurality of second openings 22. The transition between the smaller diameter of proximal end 44 and the larger diameter of proximal portion 32 preferably occurs within one of the openings of the plurality of second openings 22.

Figure 9:
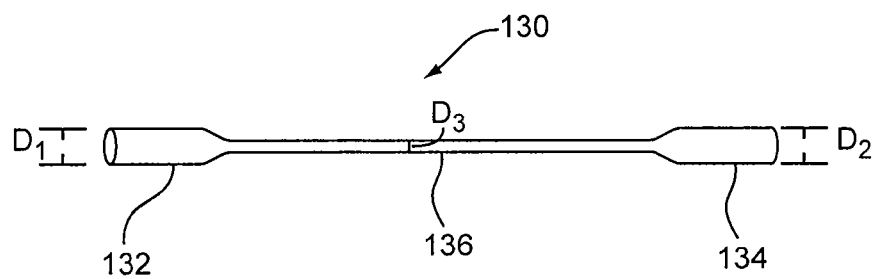
FIG. 9 is a longitudinal view of the trigger wires where the trigger wires have a larger diameter at the proximal and distal ends.

FIGS. 8 and 9 illustrate another embodiment of the self-expanding medical device delivery system 2. In this embodiment, a plurality of trigger wires 130 is connected to a handle 40 at the distal end of the self-expanding medical device delivery system 2. FIG. 5 shows a rotary handle 40, but handle 40 may be any of several well-known devices used to pull trigger wires and other elongate devices distally through a stent delivery system, including push-pull devices, rotary devices, and devices that employ a pistol grip. The handle 40 may also be configured to take up each of the trigger wires of the plurality of trigger wires 30 at different rates.

Each of the trigger wires of the plurality of trigger wires 130 has a proximal portion 132, a distal portion 134, and a center portion 136. Proximal portion 132 has a first diameter, distal portion 134 has a second diameter, and center portion 136 has a third diameter. The first diameter of proximal portion 132 is greater than the third diameter of center portion 136. The second diameter of distal portion 134 is also greater than the third diameter of center portion 136. The first diameter of proximal portion 132 may be greater than, equal to, or lesser than the second diameter of distal portion 134, depending on the diameters required to provide adequate bending strength required. As noted above, the adequate bending strength for the proximal portion 132 varies with the self-expanding medical device 24 used. The diameter of the proximal portion 132 required to retain a common stent graft may range from 2 to 5 times the diameter of the center portion 136. The proximal portion 132 of each of the trigger wires of the plurality of trigger wires 130 must be long enough to form a bend around the exposed structural members 28. For a typical stent graft, the proximal portion 132 may be 1 to 2 inches long.

Additional bending strength is required at the distal portion 134 of each of the trigger wires of the plurality of trigger wires 130 to ensure a secure connection between distal portion 134 of each of the trigger wires of the plurality of trigger wires 130 and handle 40. The adequate bending strength for the distal portion 134 varies with the handle 40 used. The length of distal portion 134 also varies based on the type of handle 40 used.

Center portion 136 of each of the trigger wires of the plurality of trigger wires 130 only requires adequate tensile strength to withdraw each of the trigger wires of the plurality of trigger wires 130 through lumen 18 of inner member 12. Thus, the required diameter of center portion 136 is less than the diameter of proximal portion 132 and distal portion 134. Each of the trigger wires of the plurality of trigger wires 130 with a decreased diameter in center portion 136 is desirable to lower the profile of self-expanding medical device delivery system 2. The center portion 136 of each of the trigger wires of the plurality of trigger wires 130 must be long enough to extend from the deployment site through the vasculature and to the distal portion 134. Thus, the center portion 136 may be up to 3 feet long.

The transition between the smaller diameter of center portion 136 and the larger diameter of proximal portion 132 preferably occurs within one of the openings of the plurality of first openings 20.

Figure 10:
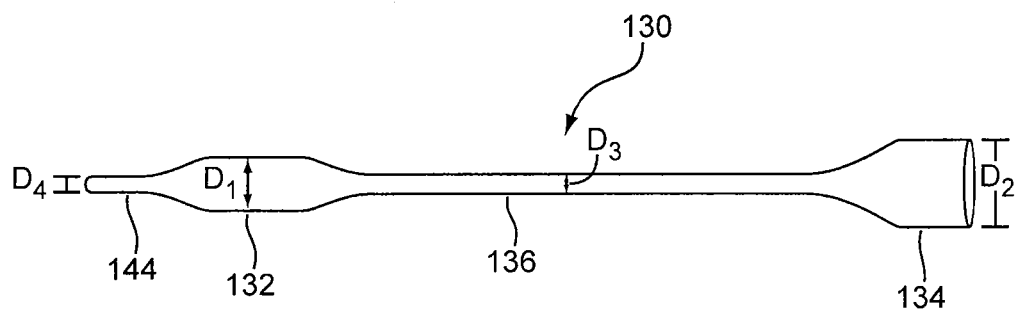
FIG. 10 is a longitudinal view of the trigger wires where the trigger wires have a smaller diameter at the proximal end and the center, and a larger diameter at the proximal and distal portions of the trigger wires.
Figure 11:
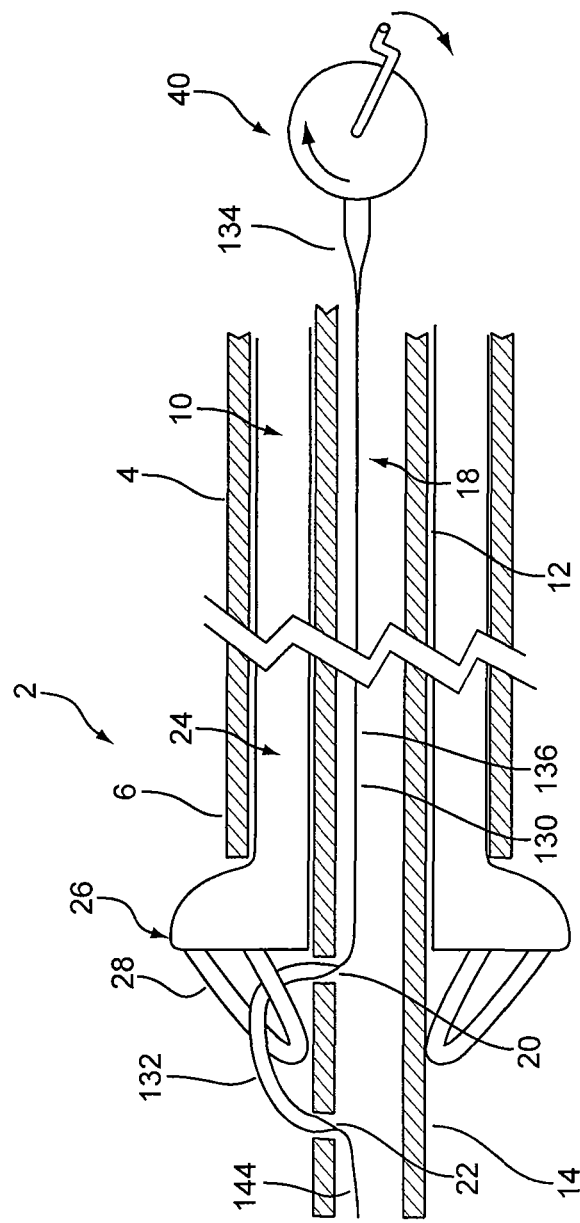
FIG. 11 is a longitudinal section view of self-expanding medical device delivery system employing the trigger wires shown in FIG. 10.

FIGS. 10 and 11 illustrate another embodiment of each of the trigger wires of the plurality of trigger wires 130. In this embodiment, each of the trigger wires of the plurality of trigger wires 130 has proximal portion 132, a distal portion 134, and a center portion 136. The proximal portion 132 has a proximal end 144. The proximal portion 132 has a first diameter, distal portion 134 has a second diameter, center portion 136 has a third diameter, and the proximal end 144 of the proximal portion 132 has a fourth diameter. The first diameter of proximal portion 132 is greater than the third diameter of center portion 136. The second diameter of distal portion 134 is also greater than the third diameter of center portion 136. The first diameter of proximal portion 132 is greater than the fourth diameter of the proximal end 144 of proximal portion 132. The first diameter of proximal portion 132 may be greater than, equal to, or lesser than the second diameter of distal portion 134, depending on the diameters required to provide adequate bending strength. The third diameter of center portion 136 may be greater than, equal to, or lesser than the fourth diameter of the proximal end 144 of the proximal portion 132, depending on the diameters required to provide adequate tensile strength.

As shown in FIG. 11, the proximal end 144 of each of the trigger wires of the plurality of trigger wires 130 is the portion of each of the trigger wires of the plurality of trigger wires 130 that re-enters inner member 12 through one of the openings of the plurality of second openings 22. The transition between the smaller diameter of proximal end 144 and the larger diameter of proximal portion 132 preferably occurs within one of the openings of the plurality of second openings 22.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A self-expanding medical device delivery system comprising:

a delivery sheath with a lumen and a proximal portion;

an inner member partially disposed within said lumen of said delivery sheath, said inner member having a lumen and a proximal portion and a distal end, said proximal portion of said inner member having a plurality of first openings and a plurality of second openings, where said plurality of second openings is disposed proximally of said plurality of first openings;

a self-expanding medical device disposed about said proximal end of said inner member, said self-expanding medical device having a proximal end, said self-expanding medical device having exposed structural members on said proximal end of said self-expanding medical device;

a plurality of trigger wires partially disposed within said lumen of said inner member, each of said trigger wires of said plurality of trigger wires having a proximal portion with a first diameter and distal portion with a second diameter, where said first diameter is greater than said second diameter, wherein the distal portion of each of said trigger wires of said plurality of trigger wires extends distally through the lumen of said inner member;

each of said trigger wires of said plurality of trigger wires exits said lumen of said inner member through one of the openings of said plurality of first openings and re-entering said lumen of said inner member through one of the openings of said plurality of second openings such that said proximal portion of each of said trigger wires of said plurality of trigger wires forms a bend, said bend engaging and retaining one of said exposed structural members such that said exposed structural members are compressed and retained by the bend, and said self-expanding medical device is retained by said proximal portion having a diameter greater than the diameter of the distal portion of each of said trigger wires of said plurality of trigger wires, wherein the diameter of the bend that retains said exposed structural member is said first diameter that is greater than said second diameter of the distal portion in order to provide adequate strength to retain said exposed structural member; and said plurality of trigger wires configured to be withdrawn in the distal direction through said lumen of said inner member such that said plurality of trigger wires disengages said exposed structural members and said self-expanding medical device.

2. The delivery system of claim 1 wherein said first diameter of each of said trigger wires of said plurality of trigger wires is 2 to 5 times greater than said second diameter of said trigger wire.

3. The delivery system of claim 1 wherein said self-expanding medical device is a stent graft.

4. The delivery system of claim 1 wherein said self-expanding medical device is a self-expanding stent.

5. The delivery system of claim 1 further comprising a guide wire partially disposed within said delivery sheath with a proximal end, said proximal end of said guide wire extending beyond the most proximal portion of said inner member.

6. The delivery system of claim 1 having a delivery configuration, wherein said proximal portion of each of said trigger wires of said plurality of trigger wires lies proximal of said plurality of first openings in said delivery configuration.

7. The delivery system of claim 1 wherein each of said openings of said plurality of first openings is positioned a different distance from said distal end of said inner member and each of said openings of said plurality of second openings is positioned a different distance from said distal end of said inner member.

8. The delivery system of claim 1 wherein said proximal portion of said inner member has a proximal end, wherein said proximal portion of said inner member is flared outward.

9. The delivery system of claim 1 wherein said proximal portion of each of said trigger wire of said plurality of trigger wires has a proximal end, said proximal end having a third diameter, wherein said first diameter is greater than said third diameter.

10. A self-expanding medical device delivery system comprising:

a delivery sheath with a lumen and a proximal portion;

an inner member partially disposed within said lumen of said delivery sheath, said inner member having a lumen and a proximal portion and a distal end, said proximal portion of said inner member having a plurality of first openings and a plurality of second openings, where each of said openings of said plurality of second openings is disposed proximally of each of said openings of said plurality of first openings;

a self-expanding medical device disposed about said proximal end of said inner member, said self-expanding medical device having a proximal end, said self-expanding medical device having exposed structural members on said proximal end of said self-expanding medical device;

a plurality of trigger wires partially disposed within said lumen of said inner member, each of said trigger wires of said plurality of trigger wires having a proximal portion with a first diameter, a distal portion with a second diameter, and a center portion with a third diameter, where said first diameter is greater than said third diameter and said second diameter is greater than said third diameter, wherein said center portion extends distally through said lumen of said inner member;

each of said trigger wires of said plurality of trigger wires exits said lumen of said inner member through one of the openings of said plurality of first openings and re-entering said lumen of said inner member through one of the openings of said plurality of second openings such that said proximal portion of each of said trigger wires of the plurality of trigger wires forms a bend, said bend engaging and retaining one of said exposed structural members such that said exposed structural members are compressed and retained and said self-expanding medical device is retained by said proximal portions having a diameter greater than the diameter of the distal portion of each of said trigger wires of said plurality of trigger wires, wherein the diameter of the bend that retains said exposed structural member is said first diameter that is greater than said third diameter of the center portion in order to provide adequate strength to retain said exposed structural member; and a handle, said distal portion of each of said trigger wires of said plurality of trigger wires connected to said handle, said handle configured to withdraw said plurality of trigger wires in the distal direction through said lumen of said inner member such that said plurality of trigger wires disengages said exposed structural members and releases said self-expanding medical device.

11. The delivery system of claim 10 wherein said first diameter of each of said trigger wires of said plurality of trigger wires is 2 to 5 times greater than said third diameter of said trigger wire.

12. The delivery system of claim 10 wherein said second diameter of each of said trigger wires of said plurality of trigger wires is 2 to 5 times greater than said third diameter of said trigger wire.

13. The delivery system of claim 10 wherein said self-expanding medical device is a stent graft.

14. The delivery system of claim 10 wherein said self-expanding medical device is a self-expanding stent.

15. The delivery system of claim 10 further comprising a guide wire partially disposed within said inner member with a proximal end, said proximal end of said guide wire extending beyond the most proximal portion of said inner member.

16. The delivery system of claim 10 having a delivery configuration, wherein said proximal portion of each of said trigger wires of said plurality of trigger wires lies proximal of said plurality of first openings in said delivery configuration.

17. The delivery system of claim 10 wherein each of said openings of said plurality of first openings is positioned a different distance from said distal end of said inner member and each of said openings of said plurality of second openings is positioned a different distance from said distal end of said inner member.

18. The delivery system of claim 10 wherein said proximal portion of said inner member has a proximal end, said proximal portion of said inner member flared outward such that said proximal end has the largest diameter.

19. The delivery system of claim 10 wherein said proximal portion of each of said triggers wires of said plurality of trigger wires has a proximal end, said proximal end having a fourth diameter, wherein said first diameter is greater than said fourth diameter.

\* \* \* \* \*